United States Patent
Vardi et al.

(10) Patent No.: US 10,512,628 B2
(45) Date of Patent: Dec. 24, 2019

(54) DINOTEFURAN LIQUID FLEA AND TICK TREATMENT

(71) Applicant: SOLANO S.P. LTD., Ram On (IL)

(72) Inventors: Amnon Vardi, Ram On (IL); Amir Kafri, Ram On (IL); Nimrod Vardi, Ram On (IL)

(73) Assignee: SOLANO S.P. LTD., Ram On (IL)

( * ) Notice: Subject to any disclaimer, the term of this patent is extended or adjusted under 35 U.S.C. 154(b) by 0 days.

(21) Appl. No.: 16/095,696

(22) PCT Filed: Apr. 24, 2017

(86) PCT No.: PCT/IL2017/050468
§ 371 (c)(1),
(2) Date: Oct. 23, 2018

(87) PCT Pub. No.: WO2017/187435
PCT Pub. Date: Nov. 2, 2017

(65) Prior Publication Data
US 2019/0125719 A1   May 2, 2019

Related U.S. Application Data

(60) Provisional application No. 62/326,756, filed on Apr. 24, 2016.

(51) Int. Cl.
| | | |
|---|---|---|
| A61K 31/341 | (2006.01) | |
| A61K 9/70 | (2006.01) | |
| A61K 9/00 | (2006.01) | |
| A61K 47/10 | (2017.01) | |
| A61K 47/32 | (2006.01) | |
| A61P 33/14 | (2006.01) | |
| A01N 25/02 | (2006.01) | |
| A01N 25/06 | (2006.01) | |
| A01N 37/34 | (2006.01) | |
| A01N 43/08 | (2006.01) | |
| A01N 47/08 | (2006.01) | |
| A01N 51/00 | (2006.01) | |

(52) U.S. Cl.
CPC ............ A61K 31/341 (2013.01); A01N 25/02 (2013.01); A01N 25/06 (2013.01); A01N 37/34 (2013.01); A01N 43/08 (2013.01); A01N 47/08 (2013.01); A01N 51/00 (2013.01); A61K 9/0017 (2013.01); A61K 9/7015 (2013.01); A61K 47/10 (2013.01); A61K 47/32 (2013.01); A61P 33/14 (2018.01)

(58) Field of Classification Search
None
See application file for complete search history.

(56) References Cited

U.S. PATENT DOCUMENTS

| | | |
|---|---|---|
| 4,933,371 A | 6/1990 | Hink et al. |
| 5,660,844 A | 8/1997 | Christie et al. |
| 5,968,990 A | 10/1999 | Jon et al. |
| 6,024,972 A | 2/2000 | Narayanan et al. |
| 6,255,350 B1 | 7/2001 | Jon et al. |
| 6,337,345 B1 | 1/2002 | Fukuchi |
| 6,372,242 B1 | 4/2002 | Gutierrez |
| 6,543,389 B2 | 4/2003 | Hedde |
| 6,588,374 B1 | 7/2003 | Cottrell et al. |
| 6,740,653 B2 | 5/2004 | Narayanan et al. |
| 6,814,030 B2 | 11/2004 | Cottrell et al. |
| 6,835,386 B2 | 12/2004 | Gutierrez |
| 6,867,233 B2 | 3/2005 | Cottrell et al. |
| 6,889,632 B2 | 5/2005 | Cottrell et al. |
| 6,984,662 B2 | 1/2006 | Cottrell et al. |
| 7,025,978 B1 | 4/2006 | Sirunyan et al. |
| 7,132,448 B2 | 11/2006 | Cottrell et al. |
| 7,345,092 B2 | 3/2008 | Cottrell et al. |
| 7,354,595 B2 | 4/2008 | Cottrell et al. |
| 7,368,455 B2 | 5/2008 | Cottrell et al. |
| 7,531,186 B2 | 5/2009 | Boeckh et al. |
| 7,855,231 B2 | 12/2010 | Cottrel et al. |
| 7,906,128 B2 | 3/2011 | Heaney et al. |
| 7,906,130 B2 | 3/2011 | Sabnis et al. |
| 7,906,535 B2 | 3/2011 | Cottrell et al. |
| 7,910,122 B2 | 3/2011 | Sirinyan et al. |
| 8,097,603 B2 | 1/2012 | Sirinyan et al. |
| 8,853,282 B1* | 10/2014 | Cottrell .............. A01N 47/44 514/461 |
| 9,622,478 B2 | 4/2017 | Vardi et al. |
| 2006/0252728 A1 | 11/2006 | Sirinyan et al. |
| 2007/0020304 A1 | 1/2007 | Tamarkin et al. |
| 2007/0078171 A1 | 4/2007 | Andersch et al. |

(Continued)

FOREIGN PATENT DOCUMENTS

| | | |
|---|---|---|
| CA | 2564234 | 11/2005 |
| EP | 1212943 | 6/2002 |

(Continued)

OTHER PUBLICATIONS

Stanneck D et al, Evaluation of the long-term efficacy and safety of an imidacloprid 10%/flumethrin 4.5% polymer matrix collar (Seresto) in dogs and cats naturally infested with fleas and/or ticks in multicentre clinical fields studies in Europe, Parasites & Vectors, 2012, pp. 1-11.

(Continued)

*Primary Examiner* — Po-Chih Chen
(74) *Attorney, Agent, or Firm* — A.C. Entis-IP Ltd.; Allan C. Entis; Kenichi N. Hartman

(57) ABSTRACT

There is provided in accordance with an embodiment of the disclosure a spray-on composition for the treatment and prevention of insect or arachnid infestation on a mammal comprising between 0.1% and 1.0% by weight dinotefuran. There is also provided in accordance with an embodiment of the disclosure a method for treatment of an animal at risk of insect or arachnid infestation comprising topically administering to the coat of the animal a composition comprising between 1 and 50 mg dinotefuran per kilogram of animal weight. Optionally, topically administering includes spraying on a majority of the area of the coat of the animal.

18 Claims, 3 Drawing Sheets

(56) References Cited

U.S. PATENT DOCUMENTS

| | | |
|---|---|---|
| 2008/0306138 A1 | 12/2008 | Zupan et al. |
| 2009/0069386 A1 | 3/2009 | Dairiki et al. |
| 2012/0071484 A1 | 3/2012 | Reynolds |
| 2013/0130908 A1 | 5/2013 | Westbye |

FOREIGN PATENT DOCUMENTS

| | | |
|---|---|---|
| JP | 08217606 | 8/1996 |
| WO | 2004089083 | 10/2004 |
| WO | 2005007140 | 1/2005 |
| WO | 2006027124 | 3/2006 |
| WO | 2006027125 | 3/2006 |
| WO | 2006027126 | 3/2006 |
| WO | 2006127407 | 11/2006 |
| WO | 2008030385 | 3/2008 |
| WO | 2008048963 | 4/2008 |
| WO | 2008098168 | 8/2008 |
| WO | 2010011596 | 1/2010 |
| WO | 2010059529 | 5/2010 |
| WO | 2010096623 | 8/2010 |

OTHER PUBLICATIONS

International Search Report dated Apr. 6, 2014 for PCT/IB2013/059385, filed Oct. 16, 2013.
International Preliminary Report on Patentability dated Jan. 11, 2015 for PCT/IB2013/059385, filed Oct. 16, 2013.
International Search Report and Written Opinion dated Jul. 6, 2017 for PCT/IL2017/050468 filed Apr. 24, 2017.
EP Search Report dated Apr. 29, 2016 for EP13847258.4, filed May 12, 2015.
VetStreet, Flea and Tick Prevention, Mar. 2014.
Eurobichon, Use of shampoos in Dogs, Jun. 13, 2007.
U.S. Office Action dated Jan. 20, 2016 for U.S. Appl. No. 14/435,455, filed Apr. 14, 2015.
U.S. Final Office Action dated Jul. 15, 2016 for U.S. Appl. No. 14/435,455, filed Apr. 14, 2015.

* cited by examiner

Table 1 First Study Group (Dogs and Cats) – Efficacy and Waterproof Study

| ID | | Weight (kg) 15.08.19 | Weight (kg) 19.09.15 | No of Pumps | Sex (M/F) | Initial | | +24 hours | | +72 hours | | +10 days | | Re-infestation D10 | +20 days | | +30 days | |
|---|---|---|---|---|---|---|---|---|---|---|---|---|---|---|---|---|---|---|
| | | | | | | Fleas | Ticks | Fleas | Ticks | Fleas | Ticks | Fleas | Ticks | | Fleas | Ticks | Fleas | Ticks |
| Dogs | 11 | 11.4 | 12.1 | 23 | M | 4 | 11 | 1 | 2 | 0 | 0 | 0 | 0 | 50 | 0 | 0 | 1 | 6 |
| | 12 | 4.5 | 6.0 | 9 | M | 9 | 4 | 0 | 0 | 0 | 0 | 0 | 0 | 50 | 0 | 0 | 0 | 0 |
| | 13 | 9.7 | 10.3 | 19 | M | 14 | 2 | 2 | 0 | 0 | 0 | 0 | 0 | 50 | 0 | 2 | 0 | 5 |
| | 14 | 8.0 | 10.0 | 16 | F | 11 | 2 | 0 | 0 | 0 | 0 | 0 | 0 | 50 | 0 | 0 | 0 | 1 |
| | 15 | 7.3 | 9.6 | 15 | F | 4 | 5 | 0 | 0 | 0 | 0 | 0 | 0 | 50 | 0 | 0 | 0 | 0 |
| | 16 | 3.0 | 4.2 | 6 | F | 3 | 3 | 0 | 0 | 0 | 0 | 0 | 0 | 50 | 0 | 0 | 0 | 2 |
| Cats | 17 | 3.1 | 3.8 | 6 | M | 10 | 4 | 1 | 0 | 0 | 0 | 0 | 0 | 50 | 0 | 0 | 0 | 2 |
| | 18 | 5.4 | 6.3 | 11 | M | 8 | 2 | 0 | 1 | 0 | 0 | 0 | 0 | 50 | 0 | 0 | 0 | 0 |
| | 19 | 2.0 | 3.2 | 4 | F | 15 | 5 | 0 | 0 | 0 | 0 | 0 | 0 | 50 | 0 | 0 | 0 | 1 |
| | 20 | 3.1 | 4.0 | 6 | F | 13 | 3 | 0 | 0 | 0 | 0 | 0 | 0 | 50 | 0 | 0 | 0 | 0 |
| | 21 | 1.5 | 2.2 | 3 | F | 17 | 5 | 2 | 0 | 0 | 0 | 0 | 0 | 50 | 0 | 0 | 0 | 0 |
| | 22 | 0.9 | 1.8 | 2 | F | 4 | 2 | 0 | 0 | 0 | 0 | 0 | 0 | 50 | 0 | 0 | 1 | 2 |
| Mean Fleas and ticks | | | | | | 9.3 | 4 | 0.5 | 0.3 | 0 | 0 | 0 | 0 | | 0 | 0.2 | 0.2 | 1.6 |
| "Solpreme Spray" Efficacy (%) | | | | | | | | 95 | 94 | 100 | 100 | 100 | 100 | | 100 | 100 | 100 | 97 |

Fig. 1

DINOTEFURAN LIQUID FLEA AND TICK TREATMENT

RELATED APPLICATIONS

The present application is a US National Phase of PCT Application No. PCT/IL2017/050468, filed on Apr. 24, 2017, which claims the benefit under 35 U.S.C. 119(e) of U.S. Provisional Application 62/326,756 filed on Apr. 24, 2016. The contents and disclosure of the above-noted applications are incorporated herein by reference.

FIELD

Embodiments of the invention relate to compositions comprising dinotefuran and methods of treatment of infestation using them.

BACKGROUND

Dogs, cats and other household pets may become infested by ectoparasites (surface dwelling parasites) known as fleas and ticks. Common fleas which affect pets include the cat flea (*Ctenocephalides felis*) and the dog flea (*Ctenocephalides canis*). Fleas tend to feed on the blood of pets causing discomfort to the animal. Fleas may also bite humans, causing irritation and potentially causing allergic reactions.

*Rhipicephalus sanguineus*, the brown dog tick, is a tick commonly found on dogs in a household setting. It has been implicated in causing diseases such as babesiosis and ehrlichiosis in dogs and diseases such as Rocky Mountain spotted fever in humans.

Other insects can be harmful to humans and mammals, such as flies.

SUMMARY

An aspect of an embodiment of the invention relates to compositions comprising dinotefuran, known chemically as 1-Methyl-2-nitro-3-((tetrahydrofuran-3-yl)methyl)guanidine. The compositions are optionally in liquid form and may be used to cure and/or prevent insect and/or arachnid infestations in animals, including, but not limited to, cats and dogs. According to an embodiment of the invention, compositions comprise between 0.1% and 1% by weight of active dinotefuran in the composition.

Dinotefuran is a nicotinic acetylcholine receptor inhibitor which acts to disrupt nervous systems of insects. Dinotefuran-comprising compositions have been disclosed in WO 2014/060960, incorporated herein by reference.

According to an embodiment of the invention, the compositions are topically applied to animals being treated. Optionally topical application may be spraying on the hair/fur of the animal. The compositions may be applied to the fur of a majority of the surface of an animal until the fur is wet.

Embodiments of the invention relate to compositions comprising dinotefuran in low doses, relative to previously known dinotefuran-containing compositions. Compositions according to embodiments of the invention are advantageous in that they have been shown to provide long-lasting, highly effective protection against fleas and ticks when applied to animals. Even after multiple washing of the animals after administration of the compositions, the compositions remain effective to prevent future infestation of the animals for a month subsequent to administration. Compositions according to embodiments of the invention have been shown to be effective and safe in treating young animals including puppies and kittens.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF FIGURES

Non-limiting examples of embodiments of the disclosure are described below with reference to figures attached hereto that are listed following this paragraph. Identical structures, elements or parts that appear in more than one figure are generally labeled with a same numeral in all the figures in which they appear. Dimensions of components and features shown in the figures are chosen for convenience and clarity of presentation and are not necessarily shown to scale.

FIG. 1 shows a data table of flea and tick counts for animals treated with a dinotefuran spray composition in accordance with an embodiment of the disclosure;

DETAILED DESCRIPTION

Figure 2A:
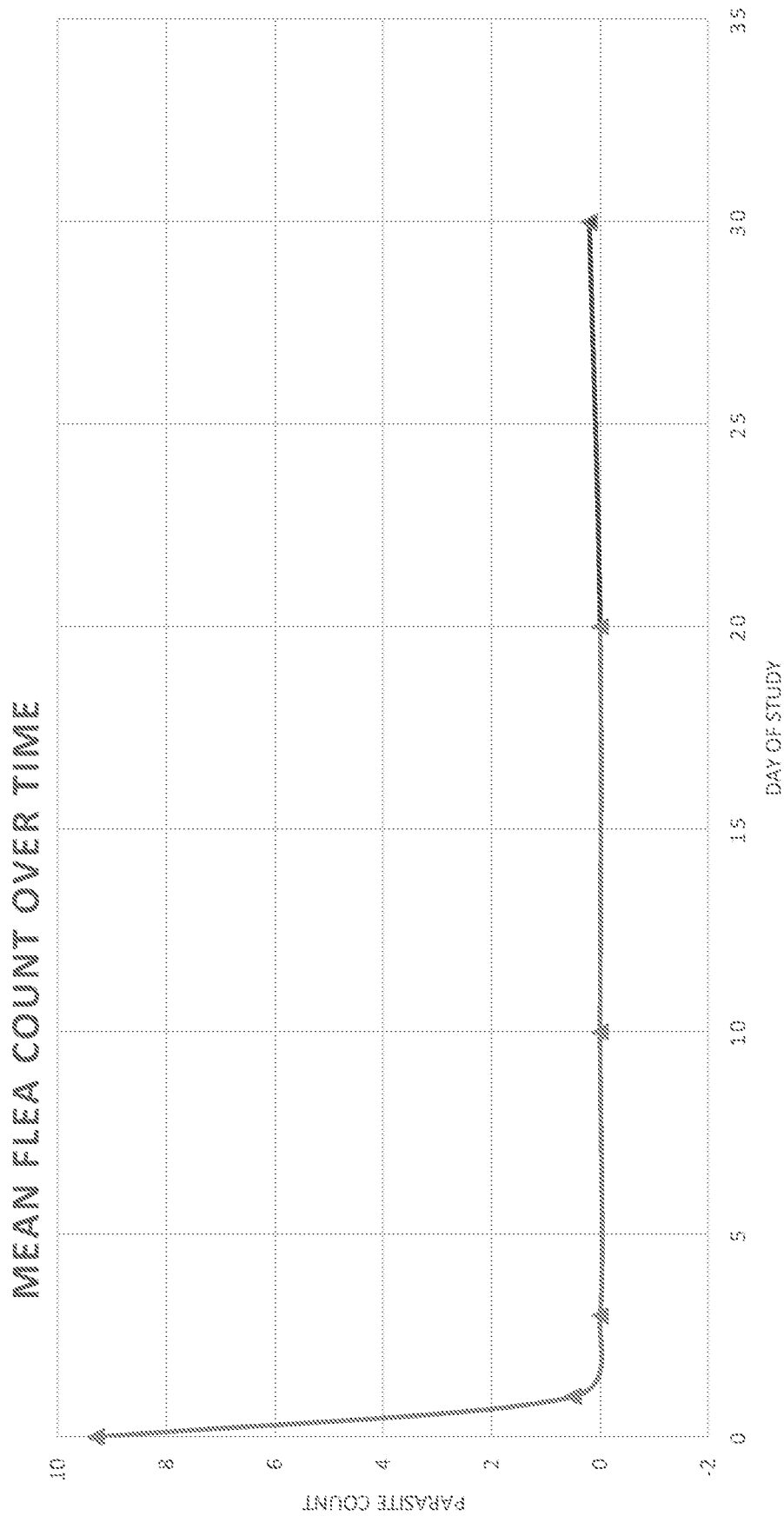
FIG. 2A shows a data plot showing mean flea counts over a 30-day course of treatment with a dinotefuran spray composition in accordance with an embodiment of the disclosure.

In the detailed description below, compositions according to embodiments of the invention, methods of their manufacture, and methods of treatment comprising using the compositions for treatment of flea and tick infestation are described.

Example 1A—Manufacture of Dinotefuran Compositions

Dinotefuran compositions are manufactured by combining the ingredients listed in table 1.

TABLE 1

| Component | Function | CAS number |
| --- | --- | --- |
| Dinotefuran | Active | 165252-70-0 |
| Isopropyl Alcohol | Solvent | 67-63-0 |
| Polyvinylpyrrolidone (PVP) | Film-forming agent | 9003-39-8 |
| Armid ® FMPC | Co-solvent | 4394-85-8 and 108-32-7 |

TABLE 1-continued

| Component | Function | CAS number |
|---|---|---|
| Butylated Hydroxytoluene (BHT) | Stabilizer | 128-37-0 |

The solvent blend Armid® FMPC is manufactured by Akzo Nobel (www.akzonobel.com) and is based on a blend of morpholine derivative with propylene carbonate. Armid® FMPC is a commercially available material comprising N-formyl morpholine (80.0% by weight) and Propylene carbonate (20.0% by weight), and is highly soluble in many other solvents such as water, propylene glycol, xylene, vegetable oil and mineral oil.

Additional dinotefuran spray-on compositions:

Alternate dinotefuran compositions according to embodiments of the invention may be prepared as described in Example 1A, with modifications as described in the following section. Compositions were prepared using the excipients in weight percent described in Table 2 below:

TABLE 2

| Component | Comp 1 | Comp 2 | Comp 3 | Comp 4 | Comp 5 |
|---|---|---|---|---|---|
| Dinotefuran | 0.25 | 0.1 | 0.5 | 0.75 | 1.0 |
| Isopropyl Alcohol | until 100 | until 100 | until 100 | until 100 | until 100 |
| Polyvinylpyrrolidone (PVP) | 2.5 | 2.5 | 0 | 5 | 0 |
| Armid ® FMPC | 2 | 0 | 5 | 5 | 5 |
| Butylated Hydroxytoluene (BHT) | 0.001 | 0.001 | 0 | 0.001 | 0 |

As shown in Table 2, compositions according to embodiments of the invention may comprise between 0.1% and 1% dinotefuran by weight. Preferred compositions according to embodiments of the invention comprise between 0.20% and 0.30% by weight dinotefuran. Preferred compositions according to embodiments of the invention comprise 0.25% by weight dinotefuran.

Alternate dinotefuran compositions according to embodiments of the invention were prepared with other solvents other than isopropyl alcohol. Other alcohols may be used in addition to or instead of isopropyl alcohol. Exemplary alcohols which may be used include alone or in combination comprise: ethanol, methanol, 1-propanol, 1,3-propanediol, benzyl alcohol, n-butanol, isobutanol, tert-amyl alcohol and 2-butanol. Table 3 lists dinotefuran compositions comprising other solvents:

TABLE 3

| Component | Comp 6 | Comp 7 | Comp 8 | Comp 9 | Comp 10 |
|---|---|---|---|---|---|
| Dinotefuran | 1.0 | 1.0 | 1.0 | 1.0 | 1.0 |
| Solvent | Benzyl alcohol until 100 | Ethanol until 100 | Methanol until 100 | Isobutanol until 100 | 2-butanol until 100 |
| Polyvinylpyrrolidone (PVP) | 2.5 | 2.5 | 5 | 2.5 | 5 |
| Armid ® FMPC | 0 | 0 | 2 | 0 | 2 |
| Butylated Hydroxytoluene (BHT) | 0.001 | 0.001 | 0.001 | 0.001 | 0.001 |

Amounts of alcohol in dinotefuran compositions according to embodiments of the invention may be used to ensure that compositions are sprayable using a pump spray bottle and that active ingredients may be dissolved in the compositions. Amount of alcohol in dinotefuran compositions may range from 50% to 98%, according to embodiments of the invention. Amount of alcohol in dinotefuran compositions may range from 90% to 96%, according to embodiments of the invention.

PVP is an alcohol-soluble polymer which in the compositions described herein, assists in adhering dinotefuran to the coat of the animal to which the compositions are being administered. In compositions according to embodiment of the invention, PVP acts as a film-forming polymer, as it assists in a film being formed on the coat of an animal after evaporation of the alcohol solvent from compositions. Other polymers suitable for use in compositions according to embodiments of the invention include, but are not limited to: polyurethane resins, cellulose acetate butyrate resins, cellulose acetate propionate resins and polyamide resin.

Amounts of film-forming polymer in dinotefuran compositions according to embodiments of the invention may be used to ensure that compositions are sprayable using a pump spray bottle and that active ingredients adhere to the coats of animals being treated. Amount of film-forming polymer in dinotefuran compositions may range from 1% to 10% according to embodiments of the invention. Amount of film-forming polymer in dinotefuran compositions may range from 2% to 5% according to embodiments of the invention. Compositions according to embodiments of the invention having varied amounts of film-forming polymer are described in Table 4.

TABLE 4

| Component | Comp 11 | Comp 12 | Comp 13 | Comp 14 | Comp 15 |
|---|---|---|---|---|---|
| Dinotefuran | 1.0 | 1.0 | 1.0 | 1.0 | 1.0 |
| Ethanol | until 100 | until 100 | until 100 | until 100 | until 100 |
| PVP | 5 | 0 | 1 | 2.5 | 10 |
| Armid ® FMPC | 5 | 5 | 5 | 5 | 2 |
| Butylated Hydroxytoluene (BHT) | 0.001 | 0.001 | 0.001 | 0.001 | 0.001 |

Armid® FMPC, as mentioned above, acts as a co-solvent to assist dissolution of dinotefuran in compositions according to embodiments of the invention. In addition to or in place of Armid® FMPC, other co-solvents may be used to assist in dissolution of dinotefuran in compositions. For example, isophorone, a cyclic ketone, and methylpyrrolidone may be used. Other combinations of N-formyl morpholine and propylene carbonate may be used as solvents in ratios other than those in Armid® FMPC such as, but not limited to, 95:5, 90:10, 75:25 and 70:30.

Compositions according to embodiments of the invention may be free of a co-solvent. Alternatively, compositions may comprise between 0% and 20% co-solvent.

Compositions according to embodiments of the invention comprising alternate co-solvents in varying amounts (or no co-solvents) are described in Table 5:

TABLE 5

| Component | Comp 16 | Comp 17 | Comp 18 | Comp 19 | Comp 20 |
|---|---|---|---|---|---|
| Dinotefuran | 0.25 | 0.25 | 0.25 | 1.0 | 0.25 |
| Isopropanol | until 100 | until 100 | until 100 | until 100 | until 100 |
| PVP | 2 | 2 | 2 | 2 | 2 |
| Co-solvent | Armid 0 | N-methyl-2-pyrrolidone 2 | Armid 2 | Armid 5 | Armid 15 |
| Butylated Hydroxytoluene (BHT) | 0.001 | 0.001 | 0.001 | 0.001 | 0.001 |

BHT is used in small quantities in compositions according to embodiments of the invention. BHT acts as a stabilizer/preservative. Alternative stabilizer may be used. A preferred amount of stabilizer is between 0.0001% and 0.01% by weight.

Compositions according to embodiments of the invention may comprise an insect growth regulator (IGR). An IGR is a compound which targets parasites during juvenile stages such as eggs and/or larvae. The IGR may be a hormonal mimetic or a chitin synthesis inhibitor. The IGR may comprise azadirachtin, hydroprene, triflumuron, pyriproxyfen and/or methoprene. The composition may comprise between 0.1% and 10% IGR. Compositions comprising insect growth regulator are described in table 6.

TABLE 6

| Component | Comp 21 | Comp 22 | Comp 23 | Comp 24 | Comp 25 |
|---|---|---|---|---|---|
| Dinotefuran | 0.25 | 0.3 | 0.25 | 0.35 | 0.3 |
| Isopropanol | until 100 | until 100 | until 100 | until 100 | until 100 |
| PVP | 2.5 | 5 | 5 | 2.5 | 5 |
| Armid ® FMPC | 2 | 0 | 1 | 1 | 0 |
| IGR | Methoprene 0.1 | Methoprene 1 | Pyriproxyfen 0.1 | Pyriproxyfen 1 | Methoprene 5 |
| BHT | 0.001 | 0.001 | 0.001 | 0.001 | 0.001 |

Synergists can be used in compositions comprising dinotefuran according to embodiments of the invention. A synergist which may be used is piperonyl butoxide (PBO). Other synergists include piperonyl sulfoxide and sesoxane. Synergists may be present in concentrations of up to 5% by weight. Synergist compositions are prepared in accordance with Table 7.

TABLE 7

| Component | Comp 26 | Comp 27 | Comp 28 | Comp 29 | Comp 30 |
|---|---|---|---|---|---|
| Dinotefuran | 0.25 | 0.3 | 0.3 | 0.25 | 0.2 |
| Isopropanol | until 100 | until 100 | until 100 | until 100 | until 100 |
| PVP | 2.5 | 5 | 2.5 | 5 | 2.5 |
| Armid ® FMPC | 0 | 1 | 2 | 4 | 4 |
| PBO | 2 | 1 | 0.1 | 0.5 | 5 |
| BHT | 0.001 | 0.001 | 0.001 | 0.001 | 0.001 |

Compositions according to embodiments of the invention may comprise flumethrin. Flumethrin may be present in the composition as an additional insecticide to act synergetically with dinotefuran. According to an embodiment of the invention, the ratio between dinotefuran (by weight) is between 4:1 and 2:1. According to an embodiment of the invention, the ratio between dinotefuran (by weight) is between 40:1 and 10:1, preferably between 30:1 and 15:1.

Example 1B: Stability Testing of Dinotefuran Compositions

Compositions described in Example A were prepared and stored in a sealed spray bottle comprising 420 milliliters (ml), at 25° Celsius (C) at 60% relative humidity. Bottle content and dinotefuran concentration were tested soon after bottling and further tested at 12, 24 and 36 months after bottling. The results indicate that the bottle content and dinotefuran concentration remained constant with a variation of less than 2% between initial observation and 36 months post-bottling.

Example 2A: Use of Dinotefuran Composition on Animals for Prevention and Treatment of Flea and Tick Infestation The studies performed in the following examples were based on EMEA/CVMP/EWP/005 "Guideline for the Testing and Evaluation of the Efficacy of Antiparasitic Substances for the Treatment and Prevention of Tick and Flea Infestation in Dogs and Cats", OPPTS 870.7200 "Companion Animal Safety"; and was performed with the approach to the OECD Principles of Good Laboratory Practice Directive 2004/10/EC and US FDA Good Laboratory Practice Regulations, 21 CFR Part 58.

The following compositions were tested on animals: a Placebo composition and a composition having 0.25% by weight dinotefuran.

Cats and dogs were used for testing efficacy of the compositions as compared with Placebo. Composition and Placebo were administered using a pump spray dispenser, dispensing 1.2 ml per pump. The animals were coated until the fur was damp to thoroughly wet. Administration amounts of Comp 1 in pumps per kilogram (kg) bodyweight, ml of composition per kg, milligram (mg) of composition per kg, and mg of active dinotefuran per kg are detailed as follows in Table 8:

TABLE 8

| Type of animal | Pumps per kilogram | ml/kg | g/kg (composition) | mg/kg (dinotefuran) |
|---|---|---|---|---|
| Short-haired animals | 2 | 2.4 | 1.9 | 4.7 |
| Long-haired or dense-coat animals | 5 | 6.0 | 4.7 | 12 |

Animals used in the study were all short-haired animals. Animals were divided into two groups, treatment group and placebo group. The treatment group consisted of 6 adult dogs and 6 adult cats. The placebo group consisted of 2 adult dogs and 2 adult cats.

Flea and ticks in the treatment and placebo groups were counted by visual observation shortly before administration and at the following intervals following administration: 24 hours, 72 hours, 10 days (prior to reinfestation) 20 days and 30 days. Visual observation for parasitic counting was performed by the same veterinarian for all animals.

Animals were also observed for clinical observations daily by a veterinarian to detect: changes in skin and fur, eyes and mucous membranes, respiratory system, circulatory system, autonomic and central nervous system, somatomotor activity, and behavior pattern. Particular attention was directed to observations of central nervous system signs (seizures, tremors, salivation), vomiting and diarrhea. All animals were individually weighed at initiation and at the end of the study.

On day 1, animals in the treatment and placebo groups were administered treatment or placebo respectively. Animals were re-infested 10 days after treatment with 50 fleas and 50 ticks each, to test the long-lasting effects of the compositions. Animals were washed once daily with water.

The efficacy of treatment was calculated as percent efficacy compared with the original flea or tick count, and was calculated according to the formula: ((mean of original flea or tick count—mean flea or tick count after treatment)/mean of original flea or tick count)×100%. Because animals were re-infested with 50 fleas after the counting at 10 days, the original flea or tick count was counted differently during the first 10 days compared to later counting days, at days 20 and 30. Up to and including the first 10 days, the original flea or tick count was the count of fleas or tick prior to treatment. Following day 10, at days 20 and 30, the original flea or tick counts was set at 50, is accordance with the number of re-infested fleas and ticks.

FIG. 1 shows a data table of flea and tick counts for the dinotefuran spray treatment group in a combined group of dogs and cats (n=12; 6 dogs and 6 cats).

FIG. 2A shows a data plot showing mean flea counts in the combined group over the 30-day course of the study The efficacy for the treatment group was at 100% after 72 hours, 10 days, and 20 days and at 99.6% after 30 days.

Figure 2B:
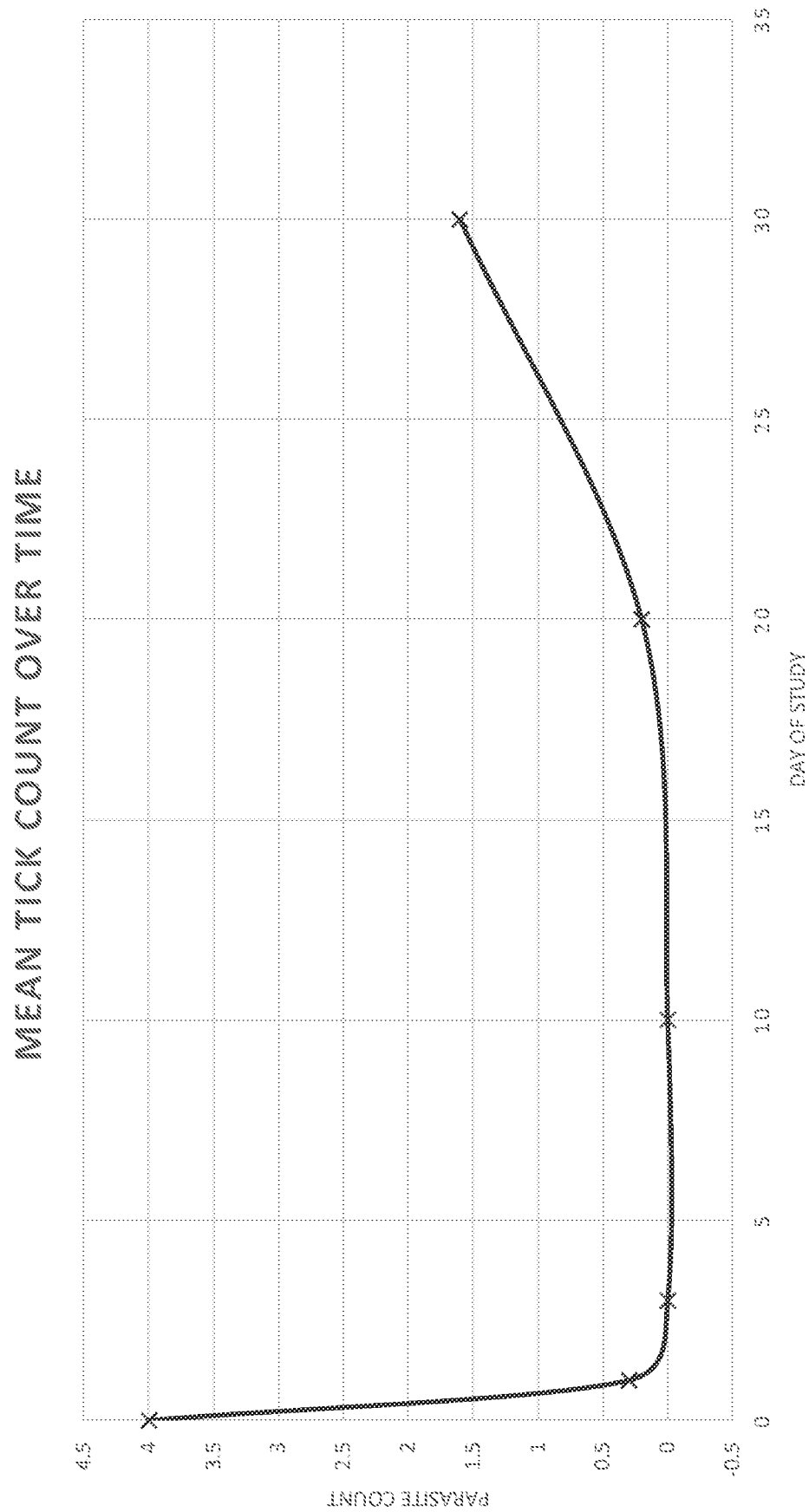
FIG. 2B shows a data plot showing mean tick counts over a 30-day course of treatment with a dinotefuran spray composition in accordance with an embodiment of the disclosure.

FIG. 2B shows mean tick counts in the same combined group of dogs and cats as in FIG. 2B (n=12; 6 dogs and 6 cats). The efficacy for the treatment group was at 100% (free of ticks) at days 3 and 10, 99.6% at day 20 and 97% at day 30.

As mentioned above, animals were re-infested at day 10 with 50 ticks and 50 fleas each. Nevertheless, the long-lasting effect of treatment prevented the fleas and ticks from remaining on the animals. This is evident from the counts at 20 and 30 days post-treatment, in which flea and tick counts were lower than at the initiation of the treatment despite the re-infestation.

No adverse reactions were found in any of the animals treated from the treatment group. The effect lasted long although the animals were washed during the trial, indicating that the tested compositions were an effective, waterproof treatment.

With respect to the Placebo group (n=4; 2 dogs and 2 cats; not shown), dogs and cats were treated with placebo as described. The number of fleas on dogs and cats in the placebo group was not significantly reduced through the 30-day course of the study. The number of ticks decreased somewhat over the course of the study, perhaps due to the daily washing (or a result of data jitter due to small sample size), but remained substantially higher than the number of ticks in the experimental group treated with the dinotefuran spray up to day 20, after which the tick count converged.

Example 2B: Safety of Dinotefuran Composition in Animals

The compositions comprising between 0.25% and 1% dinotefuran were administered to 6 dogs in a 5-fold dosage compared to the dosages administered in Example 2A (12 ml/kg) to test the safety of the active ingredient. 5-fold administration was performed by spraying on animals until wet, waiting until the animals dried, then spraying again until wet, waiting again until the animals and repeating until appropriate 5-fold amount was reached.

Dogs were weighted at the start and end of a 14 day trial. Dogs were administered Comp 1, topically, at day 0. Six dogs were tested, and of the 6 dogs, 2 were puppies. Dogs were tested according to the following parameters: changes in skin and fur, eyes and mucous membranes, respiratory system, circulatory system, autonomic and central nervous system, somatomotor activity, and behavior pattern. Particular attention was directed to observations of central nervous system signs (seizures, tremors, salivation), vomiting and diarrhea. The dog initial weight, ending weight (30 days after administration) were measured. The examinations took place on days 1, 2 and every alternate day until day 14.

A similar trial was performed in cats, rabbits and ferrets.

All animals passed the clinical observations satisfactorily. None of the animals showed signs of adverse reactions to the composition, indicating that the composition is safe, even if administered in a 5-fold excess dose. All of the dogs gained weight over the course of the trial, indicating that the composition is safe and does not cause weight loss in animals. Even puppies (having initial weight of about 0.5 kg at start of study) did not show adverse effects after administration.

Blood was sampled from all of the animals tested before administration and after 15 days. Blood samples were tested for levels of urea, creatinine, alkaline phosphatase, alanine amino transferase, aspartate amino transferase and total bilirubin. Blood was taken by venipuncture from v. cephalica antebrachii. All animal showed no significant changes in blood levels between starting the trial and after 15 days.

This study indicates that the dinotefuran compositions are safe for use and even accidental overdose 5 times the tested dosage will not negatively impact animals, including 4 types of mammals tested.

Example 2C

Testing on Horses:

Compositions comprising between 0.2% and 1% by weight dinotefuran were sprayed on to horses effected with myiasis larvae infestation. Horses were cured from the myiasis infestation after topical administration. No side effects were evident after administration.

Methods of Treatment:

Methods of treatment according to embodiments of the invention, comprise administering compositions described above to an animal in need thereof. According to an embodiment of the invention, the animal is a mammal. The mammal may be a dog, a cat, a ferret, a rabbit or a rodent. The rodent may be a rat, mouse, hamster, guinea pig, gerbil or chinchilla. The mammal may be a horse, a cow, a sheep or a pig.

The amounts of composition administered and dinotefuran administered per kg for short-haired and long-haired animals according to embodiments of the invention are tabulated below in table 9. The specific gravity of the compositions described in the tables below is about 0.79 g/ml:

TABLE 9 short haired animals:

| Composition | Animal | ml composition per kg animal | grams composition per kg animal | mg dinotefuran per kg animal |
|---|---|---|---|---|
| Comp 2 | Short Hair | 2.4 | 1.9 | 1.9 |
| Comp 1 | Short Hair | 2.4 | 1.9 | 4.7 |
| Comp 5 | Short Hair | 2.4 | 1.9 | 19 |
| Comp 2 | Long Hair | 6 | 4.7 | 4.7 |
| Comp 1 | Long Hair | 6 | 4.7 | 12 |
| Comp 5 | Long Hair | 6 | 4.7 | 47 |

According to an embodiment of the invention, methods of treatment comprise spraying the composition onto a majority of the surface area of an animal. According to an embodiment of the invention, the composition is sprayed on the entire coat of the animal, excluding the eye, mouth and nose area.

In the description and claims of the present application, each of the verbs, "comprise," "include" and "have," and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A composition for the treatment and prevention of insect or arachnid infestation on an animal comprising between 0.1% and 1.0% by weight dinotefuran and at least one film forming agent in a solvent, wherein the composition is formulated for topical administration in liquid form to the fur of the animal.

2. The composition according to claim 1 wherein the solvent comprises one or a combination of two or more of: isopropyl alcohol, ethanol, methanol, 1-propanol, 1,3-propanediol, benzyl alcohol, n-butanol, isobutanol, tert-amyl alcohol, and 2-butanol.

3. The composition according to claim 2 wherein the solvent comprises isopropyl alcohol.

4. The composition according to claim 1, wherein the film-forming agent is selected from the group consisting of: polyvinylpyrrolidone, polyurethane resins, cellulose acetate butyrate resins, cellulose acetate propionate resins and polyamide resin.

5. The composition according to claim 1 wherein the film-forming agent is present in the composition in a concentration of 1% to 10% by weight.

6. The composition according to claim 5 wherein the film-forming agent comprises polyvinylpyrrolidone.

7. The composition according to claim 1 further comprising a co-solvent.

8. The composition according to claim 7 wherein the co-solvent comprises one of or a combination of two or more of: isophorone, methylpyrrolidone, N-formyl morpholine, and propylene carbonate.

9. The composition according to claim 8 wherein the co-solvent is present in the compositions in an amount between 0.1% and 20% by weight.

10. The composition according to claim 1 comprising between 0.2% and 0.5% by weight dinotefuran.

11. A method for treatment of an animal having, or at risk of having, an insect or arachnid infestation, the method comprising topically administering to the fur of the animal a composition in liquid form comprising dinotefuran and a film-forming agent, at a dosage of between 1 mg and 50 mg dinotefuran per kilogram of animal weight.

12. The method according to claim 11 wherein the animal is selected from the group consisting of: dog, cat, ferret, rabbit, rat, mouse, hamster, guinea pig, gerbil, chinchilla, horse, cow, sheep and pig.

13. The method according to claim 11 wherein topically administering comprises spraying the composition on a majority of the area of the fur of the animal.

14. The method according to claim 11 comprising administering the composition once in a period of 30 days.

15. The method according to claim 14 further comprising washing the animal during the period of 30 days.

16. The method according to claim 11 wherein the amount administered is between 1 mg dinotefuran per kilogram of animal weight and 20 mg dinotefuran per kilogram of animal weight.

17. The method according to claim 16 wherein the amount administered is between 2 mg dinotefuran per kilogram of animal weight and 6 mg dinotefuran per kilogram of animal weight.

18. The method according to claim 11 wherein the animal has a flea or tick infestation at the time of administration.

* * * * *